US007385271B2

(12) United States Patent
McFarland et al.

(10) Patent No.: US 7,385,271 B2
(45) Date of Patent: *Jun. 10, 2008

(54) CHEMICAL SENSOR USING CHEMICALLY INDUCED ELECTRON-HOLE PRODUCTION AT A SCHOTTKY BARRIER

(75) Inventors: Eric W. McFarland, Santa Barbara, CA (US); Henry W. Weinberg, Palo Alto, CA (US); Hermann Nienhaus, Neukirchen-Vluyn (DE); Howard S. Bergh, San Francisco, CA (US); Brian Gergen, Goleta, CA (US); Arunava Mujumdar, Orinda, CA (US)

(73) Assignee: Adrena, Inc., Carpinteria, CA (US)

( * ) Notice: Subject to any disclaimer, the term of this patent is extended or adjusted under 35 U.S.C. 154(b) by 354 days.

This patent is subject to a terminal disclaimer.

(21) Appl. No.: 11/119,258

(22) Filed: Apr. 29, 2005

(65) Prior Publication Data

US 2005/0199495 A1   Sep. 15, 2005

Related U.S. Application Data

(60) Division of application No. 10/846,433, filed on May 14, 2004, now Pat. No. 7,057,213, which is a continuation of application No. 10/170,000, filed as application No. PCT/US99/29363 on Jan. 19, 2000, now Pat. No. 6,903,433.

(51) Int. Cl.
*H01L 31/00* (2006.01)

(52) U.S. Cl. ............... 257/453; 257/449; 257/E27.04; 257/471; 257/E29.048; 257/473; 257/E29.338

(58) Field of Classification Search ............... 257/54, 257/73, 260, 449, 471, 453, 473; 438/92
See application file for complete search history.

(56) References Cited

U.S. PATENT DOCUMENTS 3,513,366 A    5/1970   Clark ............... 257/484

(Continued)

FOREIGN PATENT DOCUMENTS

DE        4497477        10/1995

(Continued)

OTHER PUBLICATIONS

Electron-Hole Pair Creation at Ag and Cu Surfaces by Adsorption of Atomic Hydrogen and Deuterium by H. Nienhaus, et al.; Physical Review Letters, vol. 82, No. 2, Jan. 11, 1999; pp. 446-449.

(Continued)

*Primary Examiner*—Quoc Hoang
(74) *Attorney, Agent, or Firm*—Michael A. O'Neil

(57) ABSTRACT

Electro-hole production at a Schottky barrier has recently been observed experimentally as a result of chemical processes. This conversion of chemical energy to electronic energy may serve as a basic link between chemistry and electronics and offers the potential for generation of unique electronic signatures for chemical reactions and the creation of a new class of solide state chemical sensors. Detection of the following chemical species was established: hydrogen, deuterium, carbon monoxide, molecular oxygen. The detector (1*b*) consists of a Schottky diode between an Si layer and an ultrathin metal layer with zero force electrical contacts.

8 Claims, 5 Drawing Sheets

U.S. PATENT DOCUMENTS

| | | | |
|---|---|---|---|
| 3,550,260 A | 12/1970 | Saltich et al. | 438/501 |
| 3,757,123 A | 9/1973 | Archer et al. | 250/338 |
| 3,980,915 A | 9/1976 | Chapman et al. | 313/101 |
| 5,285,084 A | 2/1994 | von Windheim et al. | 257/77 |
| 5,285,727 A * | 2/1994 | Reams et al. | 102/202.5 |
| 5,362,975 A | 11/1994 | von Windheim et al. | 257/76 |
| 5,417,821 A | 5/1995 | Pyke | 205/775 |
| 5,554,859 A | 9/1996 | Tsukamoto et al. | 257/10 |
| 5,602,324 A | 2/1997 | Yanagida et al. | 73/23.2 |
| 5,622,877 A | 4/1997 | Ashkinazi et al. | 438/571 |
| 5,979,934 A | 11/1999 | Shirk et al. | 280/735 |
| 6,066,884 A * | 5/2000 | Krutsick | 257/484 |
| 6,184,564 B1 | 2/2001 | Gould | 257/486 |
| 6,261,932 B1 | 7/2001 | Hulfachor | 438/570 |
| 6,433,356 B1 | 8/2002 | Cahen et al. | 257/40 |
| 6,486,476 B1 * | 11/2002 | Ochiai et al. | 250/370.01 |
| 6,569,779 B1 | 5/2003 | Lundström et al. | 438/745 |
| 6,903,433 B1 * | 6/2005 | McFarland et al. | 257/471 |
| 6,998,693 B2 | 2/2006 | McFarland et al. | 257/471 |
| 7,057,213 B2 | 6/2006 | McFarland et al. | 257/109 |
| 2006/0275968 A1 | 12/2006 | Mantl et al. | 438/197 |

FOREIGN PATENT DOCUMENTS

| | | |
|---|---|---|
| DE | 19718584 C1 | 5/1997 |
| JP | 63-71648 | 4/1988 |
| JP | 6-222027 | 8/1994 |
| JP | 7-103924 | 4/1995 |
| JP | 7-239314 | 9/1995 |
| SE | 9801610 | 11/1999 |
| SE | 514042 | 12/2000 |
| WO | WO 95/10039 | 4/1995 |
| WO | WO 99/58964 | 11/1999 |

OTHER PUBLICATIONS

An ultrahigh vacuum system for the fabrication and characterization of ultrathin metal-semiconductor films and sensors by Howard W. Berg, et al.; Review of Scientific Instruments, vol. 70, No. 4, Apr. 1999; pp. 2087-2094.

Selective H atom sensors using ultrathin Ag/Si Schottky diodies by Hermann Nienhaus, et al.; Applied Physics Letters, vol. 74, No. 26, Jun. 28, 1999; pp. 4046-4048.

Ultrathin Cu films on Si(111): Schottky barrier formation and sensor applications by H. Nienhaus, et al.; J. Vac. Sci. Technol. A 17(4), Jul./Aug. 1999; pp. 1683-1687.

Morphological investigation of ultrathin Ag and Ti films grown on hydrogen terminated Si(111) by B. Gergen; J. Vac. Sci. Technol. B 18(5), Sep./Oct. 2000; pp. 2401-2405.

Chemically Induced Electronic Excitations at Metal Surfaces by Brian Gergen; www.sciencemag.org, SCIENCE, vol. 294, Dec. 21, 2001; pp. 2521-2523.

Observation of excited electrons from nonadiabatic molecular reactions of NO and $O_2$ on polycrystalline Ag by B. Gergen, et al.; Surface Science 488 (2001) 123-132.

Engineers Develop New Chemical Sensor Based on Experimental Physics Breakthrough; National Science Foundation, NSF News, Dec. 20, 2001.

* cited by examiner

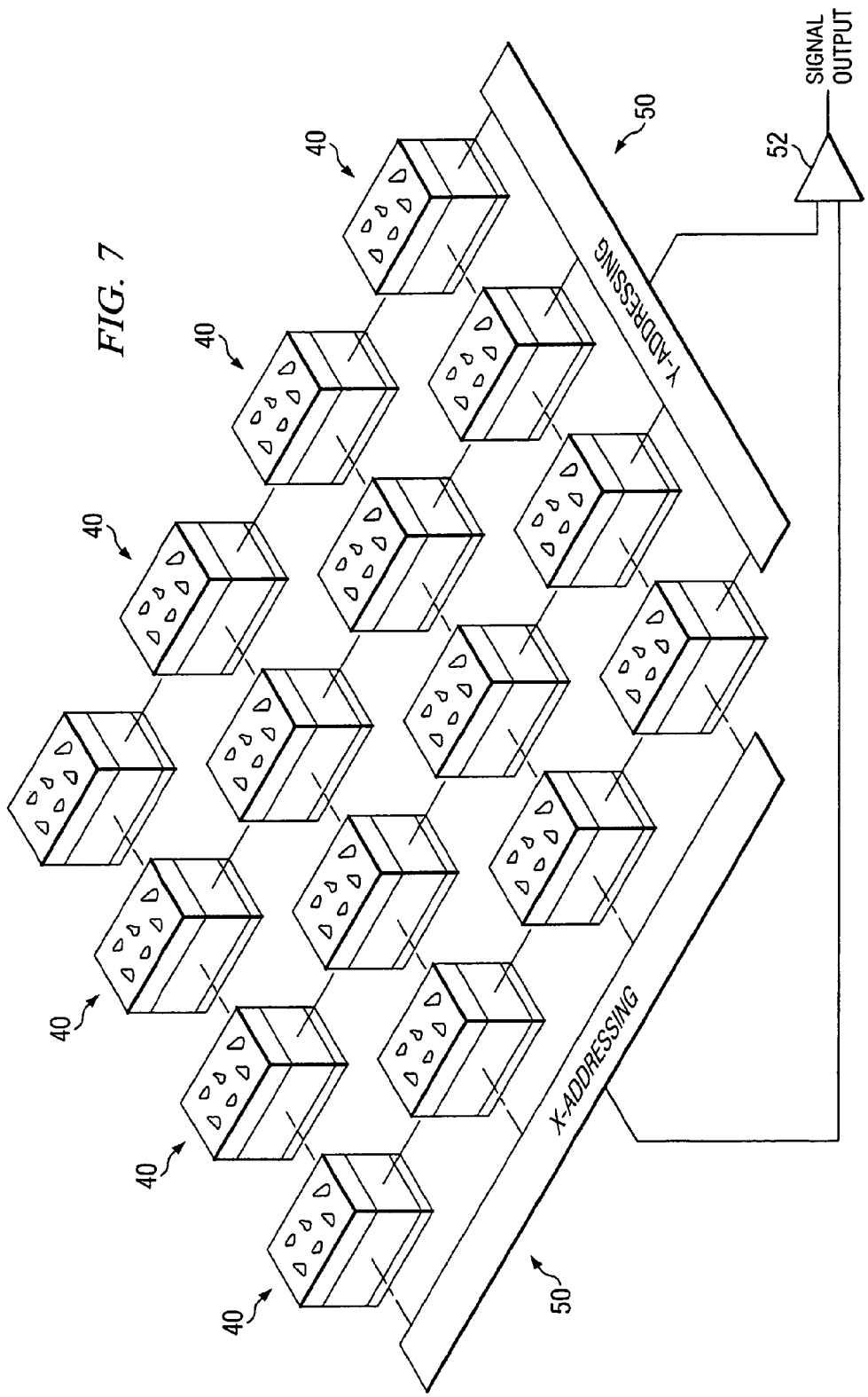

CHEMICAL SENSOR USING CHEMICALLY INDUCED ELECTRON-HOLE PRODUCTION AT A SCHOTTKY BARRIER

This application is a divisional application of application Ser. No. 10/846,433 filed May 14, 2004, now U.S. Pat. No. 7,057,213 which is a continuation application of application Ser. No. 10/170,000 filed Jul. 11, 2002, now U.S. Pat. No. 6,903,433 which is the U.S. national phase of PCT/US99/29363 filed Jan. 19, 2000.

BACKGROUND OF THE INVENTION

1. Field of the Invention

The field endeavor of the invention relates to sensors for detecting chemicals and in particular to a sensor for detecting and distinguishing atomic hydrogen or atomic deuterium oxygen, carbon monoxide, and nitric oxide.

2. Description of the Prior Art

Electron transport through a metal-semiconductor interface is determined largely by the Schottky barrier between them.

The detailed pathways of energy transfer in exothermic and endothermic reactions at a metal surface is incompletely understood and of fundamental interest. Bond formation energy of up to several electron volts is transferred into the substrate during such exothermic reactions. Since bulk phonon energies are typically two orders of magnitude smaller, it has been appreciated by the prior art that nonadiabatic excitations of electron-hole pairs may be an alternative to the creation of multiple phonons as a mechanism for sensor detectors. With surface reactions at thermal collision energies, there are few examples of energy transferring to the electronic system accompanied by light emission or chemiluminescence and exoelectron ejection. Chemiluminescence and exoelectron injection are observed only with exothermic adsorption of electronegative molecules on reactive metal surfaces. In addition, exoelectron emission requires that the metal have a low work function. Heretofore, there has been no direct experimental evidence for adsorption induced electron-hole pair excitations at transition metal surfaces.

Therefore, what is needed is some type of sensor design or principle in which adsorption induced electron hole pair excitations at a transition metal surface can be exploited to provide a chemical sensor.

BRIEF SUMMARY OF THE INVENTION

The invention is a silicon device structure, or more specifically a metal-semiconductor Schottky diode, which exploits the current-voltage characteristics of the diode for separation of charge and the interaction of the surface adsorbates on the metal to produce electrons or holes of sufficient energy to transverse the ultrathin metal film and cross the Schottky barrier. The structure allows reliable, zero force electrical contacts to be made to metal films less than 100 Angstroms thick. In one embodiment two metalized contacts are deposited using photolithographic techniques on a 4000 Angstrom oxide layer prepared on Si (111). The oxide is etched from between the contacts and the exposed 6 mm×6 mm Si (111) surface is wet chemically treated. Under vacuum conditions ultrathin metal is deposited onto the device to form a diode under well defined conditions.

The sensor device may be microfabricated on n- or p-doped semiconductor wafers. In the illustrated embodiment $p_n$=5-10 $\Omega$cm, $p_p$=1-20 $\Omega$cm, in an ohmic contact is provided on the back of a wafer by means of $As^+$ and $B^+$ ion implantation, respectively. Isolated from the silicon, the thick gold contact pads are evaporated on a 4000 Angstrom thermal oxide layer on the opposing or front side of the device. A 0.3 $cm^2$ window is chemically wet etched through the oxide layer between isolated the gold pads through the use of buffered hydrofluoric acid leaving a clean, passivated silicon surface. The device is then transferred into an ultrahigh vacuum chamber ($p \approx 10^{-8}$ Pa) for metal deposition and measurement.

Copper and silver films, for example, are deposited by e-beam evaporation at substrate temperatures of 135° K. The nominal thickness is measured by a quartz microbalance. The etching of the oxide produces an angle of inclination between the oxide and the top surface of the silicon substrate with typically 25°. The evaporated thin metal films are connected to the thick gold pads across the small inclination angle to provide a zero force front contact to the device. This contact design allows electrical contact for the current/voltage measurements between the front contacts and back contact even with film thicknesses below 80 Angstroms.

In preliminary experiments investigating the energy transfer during chemisorption, a new process has been discovered associated with chemisorption of atomic hydrogen or atomic deuterium on Ag and Cu ultrathin films. When these metals are deposited (30 Angstroms –150 Angstroms) onto Si(111) in a Schottky diode detector structure, a current is generated associated with an incident atomic H or D beam on the film. It is hypothesized that this "chemicurrent" is a result of chemisorption induced excited charge carriers which traverse the Schottky barrier. That energy transfer from chemisorption can proceed by direct electronic excitation is a significant departure from the conventional dogma which holds that multiple phonon excitation is the means through which the heat of adsorption is dissipated.

The implications of this observation for the study of surface catalyzed reactions are many. In addition, this process serves as a basic link between chemical processes and electronics and offers the potential for the generation of unique electronic signatures for chemical reactions and the creation of a new class of solid-state chemical sensor. The first direct means of measuring atomic H or atomic D separate from the diatomic molecule is demonstrated below. More importantly, it may also be possible to differentiate H from D on the basis of the signal. It is expected that there are unique chemicurrent signals associated with many types of surface reactions.

Hot electrons and holes created at a transition metal surface, such as a silver or copper surface by adsorption of thermal hydrogen and deuterium atoms can be measured directly with ultrathin-metal film Schottky diode detectors on silicon (111) according to the invention. When the metal surface is exposed to these atoms, charge carriers at the surface travel ballistically toward the interface. The charge carriers are detected as a chemicurrent in the diode. The current decreases with increasing exposure and eventually reaches a constant value at a steady state response. The invention uses the first discovery of a non-adiabatic energy dissipation during adsorption at a transition metal surface as a means of providing a chemical sensor or thin film "nose" able to sniff out the presence of chemicals.

The mechanism of the invention is based on the speculation that although the maximum energy of any hot charge carriers are smaller than the metal work function of the transition metal surface thereby precluding exoelectron emission, the energy of the hot-charged carriers may be sufficiently large enough to enable the charge carriers to be collected by crossing a smaller potential barrier. As will be described below the direct detection of chemisorption-induced electron-hole pairs is feasible using a Schottky barrier by transition metal-semiconductor diode detector. The invention shall be described in terms of an atomic hydrogen adsorption on copper and silver film surfaces, however, it is to be expressly understood that many other chemical molecules or elements may be detectable on these and other different thin film metal surfaces according to the teachings of the invention. Silver and copper film surfaces exhibit high reactivity to atomic hydrogen, but negligible disassociative adsorption of molecular hydrogen, $H_2$. The formation energy of the hydrogen-metal bond is large, about 2.5 electron volts in both cases. To detect the hot charged carriers, a sensor is provided which is comprised of a large area of metal-semiconductor contact with an ultrathin metal film.

The device structure allows current-voltage curves to be measured from which Schottky barrier heights and ideality factors as a function of metal film thickness can be determined. It is observed that barrier heights increase and ideality factors decrease with increasing metal film thickness (10 Angstroms to 100 Angstroms). Room temperature annealing of diodes produced with a low temperature metalization increases the measured barrier heights and lowers the ideality factors. The magnitude of these effects depends on the metal used. Results for iron and copper on silicon (111) substrates are among the embodiments described below.

The rectifying properties of the Schottky diode formed are improved by annealing the devices to room temperature and cooling back to 135° K. The measured I-V curves can then be analyzed using thermionic emission theory. Effective barrier heights of 0.6-0.65 electron volts and 0.5-0.55 electron volts were determined for copper and silver films of 75 Angstrom thickness on n-silicon (111), respectively. On p-silicon (111), silver and copper diodes showed barriers of 0.5-0.6 electron volts. Ideality factors between 1.05 and 1.5 indicate that large-area diodes are laterally nonuniform and exhibit a barrier height distribution.

The invention now having been briefly summarized turn to the following drawings wherein like elements are referenced by like numerals.

BRIEF DESCRIPTION OF THE DRAWINGS

FIG. 7 is an array of sensors of the type shown in FIG. 10 in which each one of the sensors has a different catalytic layer so the corresponding sensor detects a different reactant.

The invention now having been illustrated in the foregoing drawings, the invention and its various embodiments now may be understood in context in the following detailed description.

DETAILED DESCRIPTION OF THE PREFERRED EMBODIMENTS

Electron-hole production at a Schottky barrier has recently been observed experimentally as a result of chemical processes. This conversion of chemical energy to electronic energy may serve as a basic link between chemistry and electronics and offers the potential for the generation of unique electronic signatures for chemical reactions and the creation of a new class of solid state chemical sensors. The initial results have been for an atomic and molecular adsorption, however, it is also expected that bimolecular surface catalyzed reactions may also cause direct excitation of charge carriers during the formation of bonds between surface adsorbed species. Therefore, in addition to the demonstrated detection of hydrogen, deuterium and oxygen, sensitivity for chemisorption for carbon monoxide, carbon dioxide, molecular and atomic oxygen, molecular and atomic nitrogen, nitrogen monoxide and organic hydrocarbons and other species is expected. Detector responses to surface catalyzed reactions of several different combinations of these species following adsorption are expected to produce a chemicurrent including reactions with the combinations of carbon monoxide and molecular oxygen, carbon monoxide with nitrogen oxide and molecular hydrogen and oxygen. The basic configuration of the detector can be extended to include selective coatings, multi-juncition arrays, and tunnel junctions.

Figure 1A:
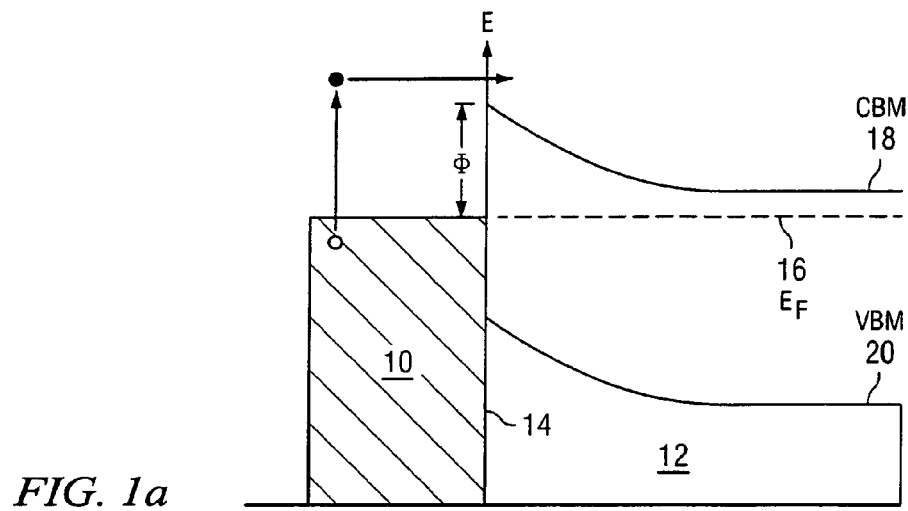
FIG. 1(a) is a Fermi diagram of the chemicurrent detection. Hydrogen atoms react with the metal surface creating electron-hole pairs. The hot electrons travel ballistically through the film into the semiconductor where they are detected.
Figure 1B:
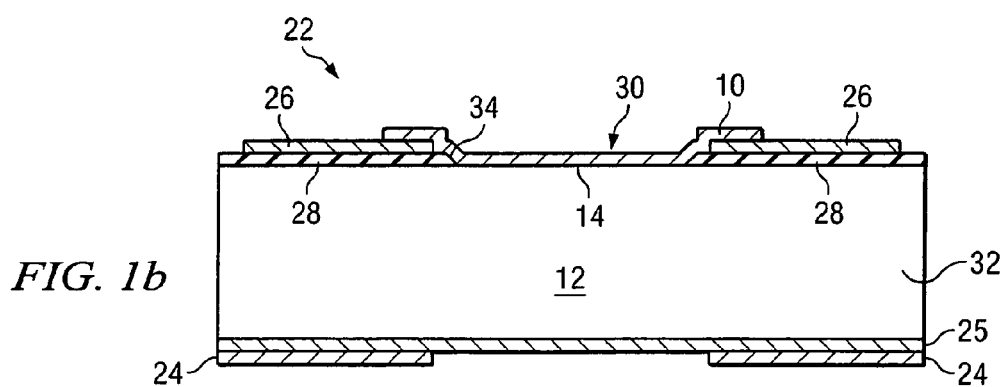
FIG. 1(b) is a schematic side cross-sectional view through a hydrogen sensing Schottky diode made according to the invention as described by the Fermi diagram of FIG. 1(a). The ultrathin metal film is connected to the gold pad during evaporation.
Figure 1C:
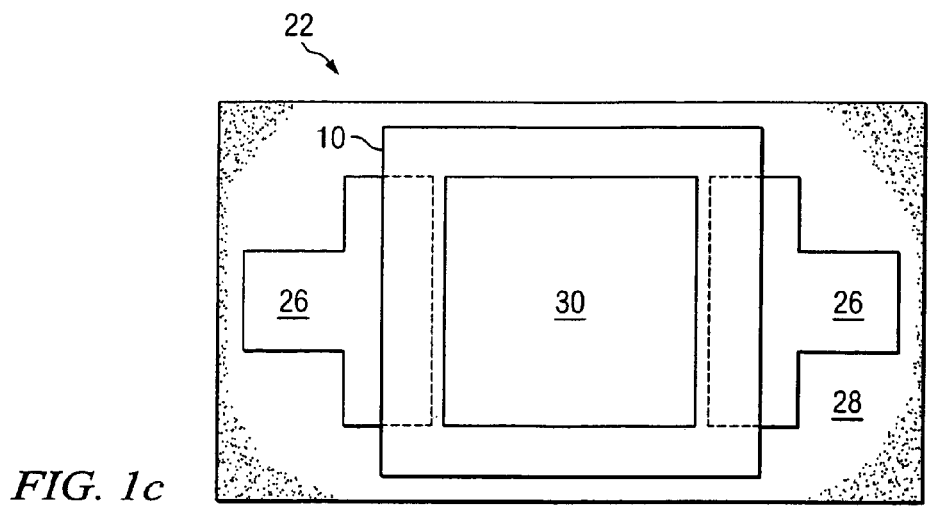
FIG. 1(c) is a plan elevational view of the device of FIGS. 1(a) and 1(b).

The mechanism of current production in a sensor is best illustrated in FIG. 1(a) in the case of hot electrons. FIG. 1(a) is an energy diagram of a charge carrier across the metal film to a silicon interface with the position in the interface being shown on the horizontal axis and energy on the vertical axis. FIG. 1(b) is a corresponding side cross-sectional view in an enlarged scale of the junction which is grafted in FIG. 1(a). FIG. 1(c) is a plan elevational view of the device of FIGS. 1(a) and 1(b). Transition metallization film layer 10 is evaporated on an n-type silicon substrate 12 forming a diode at their interface 14 with a Schottky barrier Φ illustrated in FIG. 1(a). FIG. 1(a) shows the Fermi level, EFI also denoted by reference numeral 16, the conduction band minimum, denoted by reference numeral 18 and the valence band minimum denoted by reference numeral 20. If the exothermic chemisorption of hydrogen atoms creates electron-hole pairs, hot electrons may travel ballistically through metallization film layer 10 and across the potential barrier of the Schottky diode Φ. The electrodes can be detected as a current which is defined as the "chemicurrent." Similarly, hot holes may be measured with a p-type electrode as well as an n-type as shown in the illustration of FIGS. 1(*a*) and (*b*). The charge carrier energies lie between the barrier height and the adsorption energy, i.e., between 0.5 and 2.5 electron volts above $E_F$ 16. The mean free path (mfp) of electrons and holes in this energy range is typically on the order of 100 Angstrom, as determined by thermal and field emission, internal photoemission and ballistic electron emission microscopy. The film thickness is in the range of the mean free path of the charge carriers (electrons or holes).

A silicon based device 22 was developed to facilitate contacting extremely thin metallization film layers 10 during the initial Schottky barrier formation. Devices 22 were prepared on silicon (111) substrates 12 and processed using conventional silicon microfabrication techniques to produce the device depicted in FIGS. 1(*a*), 1(*b*) and 1(*c*). Microfabricated silicon substrates 12 were made from 3" diameter 5 Ω-cm phosphorous doped n-type Si (111) wafers. Before processing, the wafers were backside ion implanted with $10^{15}$ $cm^{-2}$ zarsenic at 150 keV. After implantation the wafers were diced into rectangular samples 0.45-x0.70". The samples were then cleaned by sonication in water, acetone and isopropanol and were wet oxidized in a tube furnace to grow between 3000 and 4000 Angstroms of thermal oxide. For the processing of the substrates, AZ5214 image reversal photoresist was used as a positive resist. Two photolithographic masks were used, one for front metal contact pads 26 and one for oxide window 30 between pads 26. The first step of the processing was to metalize front contact pads 26. An oxidized silicon substrate 12 was spin coated with photoresist and patterned using a UV mask aligner. Metal pads 26 were deposited in a thermal evaporator using an initial adhesion layer of 100 Angstroms chromium followed by 2000 Angstroms of gold. After metalization, the excess metal was removed in an isopropanol sonication lift-off. This completed front contacts 26 and the next step was to make back ohmic contacts 24. The ion implantation was activated during the thermal oxidation so that under backside oxide 25 of silicon substrate 12 was n+. Front side 32 of substrate 12 was coated with a protective photoresist layer and backside oxide 25 was removed with buffered hydrofluoric acid, HF. The backside metalization was done through an aluminum shadow mask. Back contacts 24 were Cr (100 Angstroms)/Au (3000 Angstroms) and deposited in a thermal evaporator. To complete the backside metalization, the front side photoresist was removed in an isopropanol sonication. The final step of the processing was to etch a window 30 in the $SiO_2$ layer 28 between front contact pads 26. The sample was recoated with photoresist and patterned with the mask aligner. The photoresist was developed and the exposed oxide region was removed with a six minute buffered HF dip. After this step the photoresist was removed by 85° C. $H_2O_2$: $H_2SO_4$ solution. The sample was subsequently cleaned and chemically oxidized in a fresh $H_2O_2$: $H_2SO_4$ solution at 110° C. The final step was to prepare the silicon surface. After removal from the sulfuric acid, the sample was dipped in buffered HF for 15 seconds, which was just long enough to ensure removal of the chemical oxide off the silicon surface. The sample was finally rinsed in deionized water and blown dry with nitrogen to complete the processing. Because of the etching properties of the buffered HF solution and the photoresist, the resultant oxide had a gentle slope of 15-20 degrees from the unetched $SiO_2$ down to the silicon substrate. This angle was independently measured by a scanning electron microscope (SEM) and an atomic force microscope (AFM). Sloping oxide sidewall 34 allows thin Schottky metallization film layer 10 to connect continuously from one gold contact pad 26 to the other.

After the final buffered HF dip to prepare a hydrogen terminated and passivated surface, microfabricated silicon substrate 12 was quickly indium bonded to a molybdenum sample holder and loaded into an ultrahigh vacuum chamber onto a sample manipulator (not shown). The manipulator has four independent electrical contacts, two front and two back contacts. The two front contacts can be actuated from outside the vacuum chamber and were used to electrically contact gold contact pads 26 on the right and left sides of silicon substrate 12 while the back contacts 24 contact the molybdenum sample holder. After a sample was in place on the manipulator, it was checked for contact-to-contact current leakage. All samples used for experiments had room temperature left-front-contact to right-front-contact resistance greater than 100 MΩ and front-to-back resistances greater than 10 MΩ.

Metallization film layers 10 were evaporated by shuttered electron-beam wire evaporators. The evaporation rate depended on the metal used. In the embodiment where iron was used, iron was evaporated at 10 watts with a rate of 10 Angstroms $min^{-1}$, and copper was evaporated with a heating power of 16 watts and a rate of 1.5 Angstrom $min^{-1}$. The evaporator produced a collimated flux that deposited a rectangular area of metal onto silicon substrate 12. Evaporated metallization film layer 10 spanned metal contact pads 26 on either side of silicon substrate 12, but did not extend out to the edge of silicon substrate 12.

Diodes were made on room temperature substrates as well as substrates cooled to 130° K with liquid nitrogen. A Labview virtual instrument (VI) was used to automate current-voltage measurements. The voltage source was a digital-to-analog board controlled by the computer and the current was measured with a Kiethley picoammeter under GPIB control from the computer.

In the present demonstration of device 22, device 22 was maintained at 135° K. and exposed to a modulated, thermal hydrogen beam produced by a microwave plasma. Photons are extracted from the beam to avoid photoexcitation which can be orders of magnitude stronger than the chemicurrent. A light blocking fixture was developed for the plasma tube which prevents photon transmission and thermalized the beam particles as is described in H. Nienhaus, et al., *Photon Shield for Atomic Hydrogen Plasma Sources*" J. Vac. Sci. Tech., A 17 (2), pp. 670-672, 1999. The content of atomic hydrogen, $C_H$, i.e., the number of atoms relative to the total number of particles in the beam, was measured with an in-line mass spectrometer. It varied typically between 7-25% where the variations were associated with the plasma fluctuations. The kinetic energy of the atomic hydrogen was also measured between 300° K and 350° K. The total atomic and molecular hydrogen impinging upon silicon based device 22 was approximately constant, e.g., about 1013 particles per second. Hence, with a sensor area of 0.3 $cm^2$, the atomic flux varied between 3 and $10 \times 10^{12}$ hydrogen atoms per $cm^2$-second. The reaction-induced chemicurrent was detected between the front contact 26 and back contact 24 using standard lock-in techniques. No bias was applied to silicon based device 22 during measurement. Due to the low temperature, the noise level was less than 0.5 picoamps.

Figure 2A:
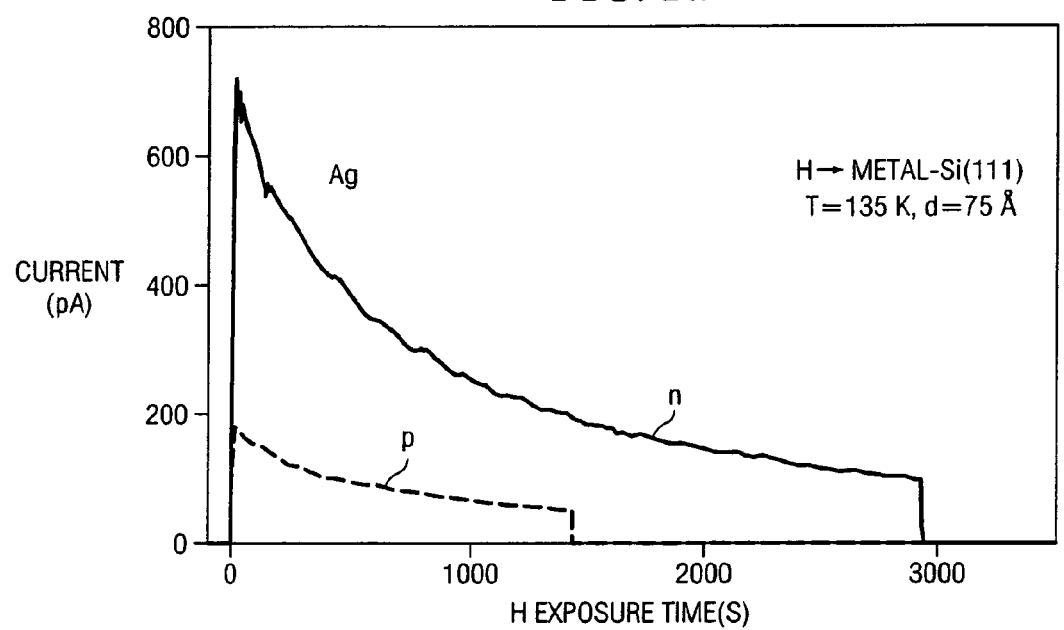
FIGS. 2(a) and 2(b) are graphs of the chemicurrent as a function of hydrogen exposure time for diodes with thin silver and copper films respectively in a device shown in FIGS. 1(a) and 1(b). The transients correspond to the filling of empty adsorption sites by atomic hydrogen on the metal surfaces. The steady-state currents are explained by a balance of abstraction and re-adsorption of atomic hydrogen.
Figure 2B:
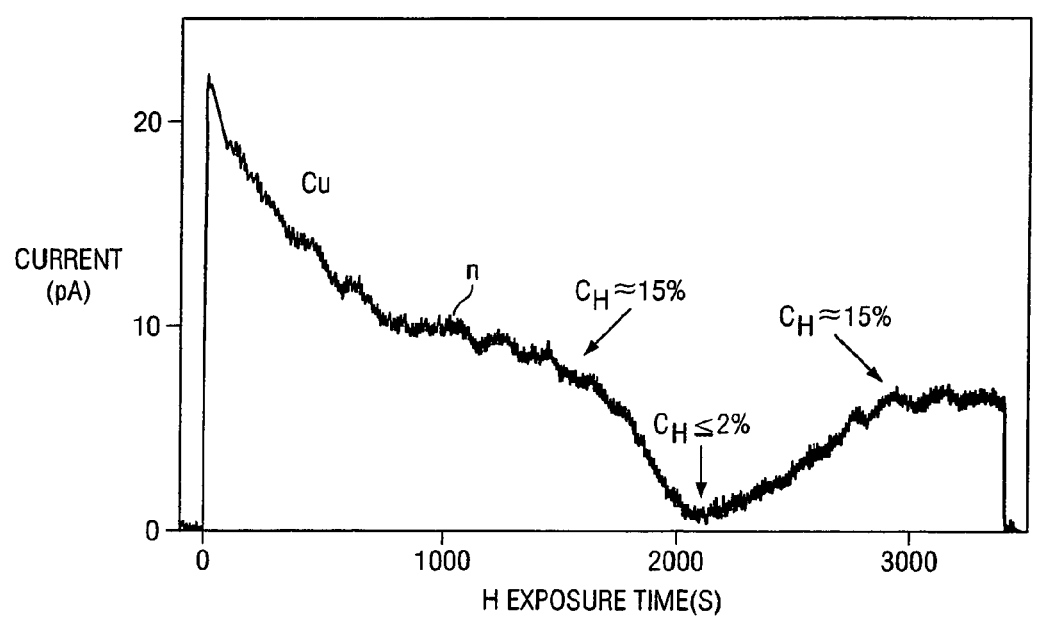

Detector current responses as a function of time of device 22 in response to atomic hydrogen are shown in FIG. 2 in which the chemicurrent is mapped against exposure times. FIG. 2(*a*) is a graph showing the chemicurrent in silver/*n*- silicon, interface and a silver/p-silicon interface. FIG. 2(b) shows the chemicurrent for a copper/n-silicon diode. The atomic impingement rate, qH, was 7.5±2.5×10$^{11}$ atoms per second. At t=0, the beam shutter was opened. Current increases instantaneously upon exposure and decays exponentially, and eventually reaches a steady state of value as shown in FIGS. 2(a) and 2(b) at each of the diode embodiments. The dip observed in the I/t curve for copper at about 2,000 seconds is due to a decrease in atomic hydrogen flux due to plasma instabilities. The atomic hydrogen content, CH1, decreases from 15% at t=1600 seconds to below the detection limit of 2% at t=2,100 seconds in FIG. 2(b). The chemicurrent then recovers its original value. The total beam intensity, atomic and molecular hydrogen remained constant during this time. Thus, chemicurrent is only detected if atomic hydrogen is present. FIG. 2(a) shows that chemicurrents were detected for both p- and n-type silver/silicon diodes, thereby implying that both hot electrons and hot holes are created by the reaction.

The chemicurrent transient shown in FIGS. 2(a) and 2(b) represents the occupation of empty adsorption sites by atomic hydrogen on metallization film layer 10. The hydrogen coverage, Θ, increases and the adsorption probability decreases with the decreasing availability of empty sites. The steady-state chemicurrent observed in the long time limit in FIGS. 2(a) and 2(b) is a consequence of a balance between hydrogen removal from the surface by abstraction and re-adsorption. The chemicurrent, I, is expected to be proportional to the hydrogen atom flux and the fraction of unoccupied adsorption sites, i.e., I=αq$_H$(Θ$_s$-Θ), where Θ$_s$ is the saturation coverage if no abstraction occurs and α is a constant.

If the adsorption of atomic hydrogen and its abstraction by atomic hydrogen in the gas phase are governed by the Langmuirian and an Eley-Rideal mechanism, respectively, the time rate equation for I and Θ obey a first-order kinetics described by:

$$dI/dt \propto -d\Theta/dt = -(q_H/A)[\sigma_a(\Theta_s, -\Theta) - \sigma_t\Theta],$$

where A is the active diode area, and $\sigma_a$ and $\sigma_t$ are the cross sections for adsorption and abstraction, respectively. By considering the time limits for t=0 and t→infinity, the ratio of the cross sections may be determined from the maximum value, $I_{max}$, and the steady state value, $I_s$ of the chemicurrent via $\sigma_a/\sigma_r = I_s/(I_{max}-I_s)$. Cross section ratio is calculated from the data in FIGS. 2(a) and 2(b) are 0.2 for the silver/n-silicon diode and 0.4 for the two other diodes. Equation (1) above predicts an exponential decay of the chemicurrent with a time constant of $A/q_H(\sigma_a+\sigma_t)$. Single exponential fits to the data in FIG. 2 result in decay constants of 480 seconds for the silver/p-silicon diode, 670 seconds for the copper/n-silicon diode, and 750 seconds for silver/n-silicon diode. The observed variation is within the range of uncertainties of the beam flux. The cross section ratio and decay constant allow the calculation of an absolute cross section if the active diode area, A, and the hydrogen atom rate, $q_H$ are known. With an active area A=to about 0.3 cm$^2$, the analysis gives values for $\sigma_a$ of approximately 5×10$^{-16}$ cm$^2$ for silver and 4×10$^{-16}$ cm$^2$ for the copper film. With assumed initial adsorption probability of unity, the reciprocal of the cross section $\sigma_a$ is equal to the adsorption site density. From the data, in FIGS. 2(a) and 2(b), the adsorption site densities of 2-3×10$^{15}$ cm$^{-2}$ for both, silver and copper films obtained. These values are in excellent agreement with the number of metal atoms per unit area which is about 2.4×10$^{15}$ cm$^2$ for silver on (111 silicon) and 3.1×10$^{15}$ cm$^2$ copper on silicon (111) surfaces. This data supports the interpretation of the I/t curves of FIGS. 2(a) and 2(b) given above. Furthermore, the data shows a new way of measuring self-abstraction rates with only one atomic species. In the prior art, the abstraction of atomic hydrogen at surfaces is studied by deuterium-hydrogen or hydrogen-deuterium exchange reactions.

The chemicurrent is attenuated exponentially with increasing metal thickness in the silver/n-silicon diodes. The attenuation length correlates well with the mfp of electrons in silver, which further supports the idea that the charge carriers are created at the metal surface and travel ballistically through the metal film into silicon substrate 12.

The quantitative difference between the n-type silver and copper Schottky diodes shown in FIGS. 2(a) and 2(b) is striking. The sensitivity may be defined by dividing the initial chemicurrent at t=0 by the hydrogen atom impingement rate. This gives the number of electrons detected per adsorption event as 4.5×10$^{-3}$ for silver and 1.5×10$^{-4}$ for copper, an order of magnitude difference. On p-type diodes, the same sensitivity ratio is found. Thus, the difference does not correspond to a barrier height difference, which is only observed with n-type Schottky diodes. The sensitivity difference is the standard attributed to two effects. First, the mfp electrons and copper films have been measured to be half that of mfp and silver films. Second, the interface properties of silver/silicon and copper/silicon are very different, e.g., the copper reacts with silicon and may form a silicide while similar reactions are not known for silver on silicon. Since the diodes are annealed, copper/silicon interfaces are expected to be rougher and have more scattering centers than silver/silicon interfaces. The enhanced roughness may reduce the transmission probability considerably, in agreement with reported results on mfp in silicides which are smaller than in metals.

The p-type silver/silicon diodes seen in FIG. 2(a) are approximately 3.5 times less sensitive than an n-type device. These might be explained by differences in the mfp path of holes and electrons in silver, as observed previously in gold and in platinum silicon thin films. In these prior art observations, the attenuation lengths of holes were a factor of approximately 1.5 times smaller than for electrons. Additionally, sensitivity differences may be related to the energy spectra of holes and electrons excited by the surface reactions. The d-bands of bulk silver cannot contribute to the ballistic current, since they are more than 2.7 electron volts below the Fermi energy. The ballistic charge carriers thus have nearly a free SP character. The probability of exciting an electron-hole pair is assumed to depend on the joint density of states of occupied and empty electronic states. Since the density of states of silver increases slightly with energy in the range of ±3 electron volts around the Fermi energy, electrons closer to the Fermi energy are excited more effectively. Consequently, the energy distributions of ballistic holes and electrons are not symmetric around the Fermi energy and on the average the ballistic electrons are expected to have higher kinetic energies than hot holes. Such an asymmetry would lead to a significant sensitivity difference between p- and n-type diodes.

Figure 3:
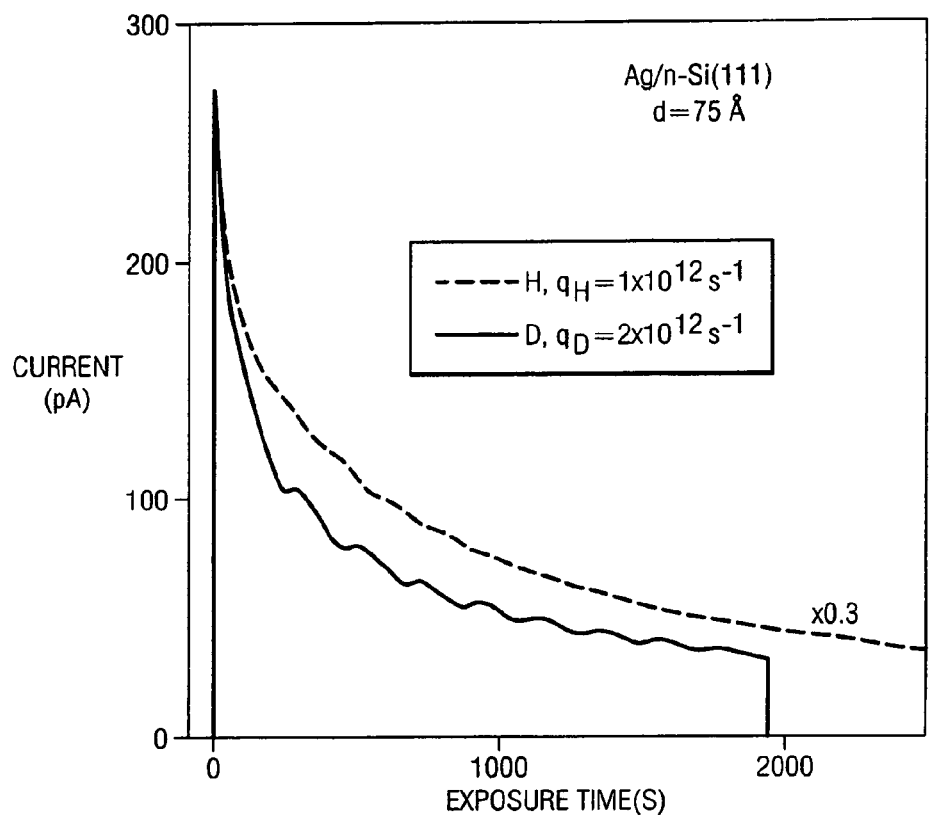
FIG. 3 is a graph of the chemicurrent, I, as a function of time, t, recorded from silver/n-Si (I 11) diodes of the type shown in FIGS. 1(a) and 1(b) exposed to atomic hydrogen and deuterium. The chemicurrent due to atomic hydrogen adsorption is multiplied by a factor of 0.3.

FIG. 3 is a graph of the chemicurrent as a function of time for atomic hydrogen and deuterium reacting with a 75 Angstrom silver film on n-silicon (111). The oscillations in the decay curve for deuterium are due to plasma fluctuations. Although for the exposure graph of FIG. 3 the impingement rate of atomic deuterium was approximately twice as large as that for atomic hydrogen, the measured chemicurrent with deuterium exposure was smaller by a factor 3, i.e., a sensitivity to atomic deuterium is six times smaller than that to atomic hydrogen. The slight differences in the strengths of hydrogen and deuterium metal bonds cannot explain this observed isotope effect. A reduced adsorption probability for deuterium on silver would also not account for this observation, since this would affect the decay rate as well. The decay rates in FIG. 3 differ by a factor of approximately 1.8 which may be exclusively attributed to the flux difference between hydrogen and deuterium. The isotope effect implies different velocities and interaction times of the incoming hydrogen and deuterium by a factor of $v^2$. The interaction time, however, is still in the $10^{-13}$ second range which is at least an order of magnitude longer than time constants of electron transfer between the substrate and the impinging atoms. For the same reason, we exclude internal exoelectron emissions which requires quenching of resonant charge transfer into the affinity level of the approaching atom accompanied by a drastic change of the surface oxidation state.

It is believed that the more relevant mechanism behind the isotope effect is likely to be the de-excitation of highly excited vibrational states formed under chemisorption. The transition probability between two vibrational levels in a nonharmonic potential decreases the larger the difference of the two respective quantum numbers. Hence, de-excitation most likely occurs in multiple steps. The spacing between the vibrational levels, ie., the density of states of vibrational states, determines the released energy in each step, and the states in the enharmonic deuterium-silver potential are closer to each other than for the hydrogen-silver bond. Since the formation energies of deuterium-silver and hydrogen-silver bonds are almost identical, the deuterium-silver vibrational energy may be relaxed in more steps of smaller energy quanta compared to the hydrogen-silver case. This would result in ballistic charge carriers of lower energies and explain the smaller sensitivity to deuterium.

In summary, the foregoing disclosure is the first direct detection reported of hot electrons and holes excited by adsorption of atomic hydrogen deuterium on ultrathin silver and copper films as a chemicurrent. The current is measured in the large-area Schottky diode formed from these metals on oriented silicon (111). The devices are unique sensors that can discriminate atomic from molecular hydrogen as well as deuterium from hydrogen atoms. The chemicurrents decay exponentially with exposure time and reach a steady-state value. This behavior corresponds to occupation of free adsorption sites by hydrogen atoms and a balance between adsorption and abstraction. The currents are smaller if p-type semiconductors are used and if the devices are exposed to deuterium rather than hydrogen. This isotope effect opens a new way of monitoring reactions on metal surfaces and will certainly initiate further investigations to clarify the mechanism of the excitation. We have developed a reliable device structure for the fabrication of ultrathin Schottky diodes.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention which could be more broadly or narrowly defined later by patent claims.

Figure 4:
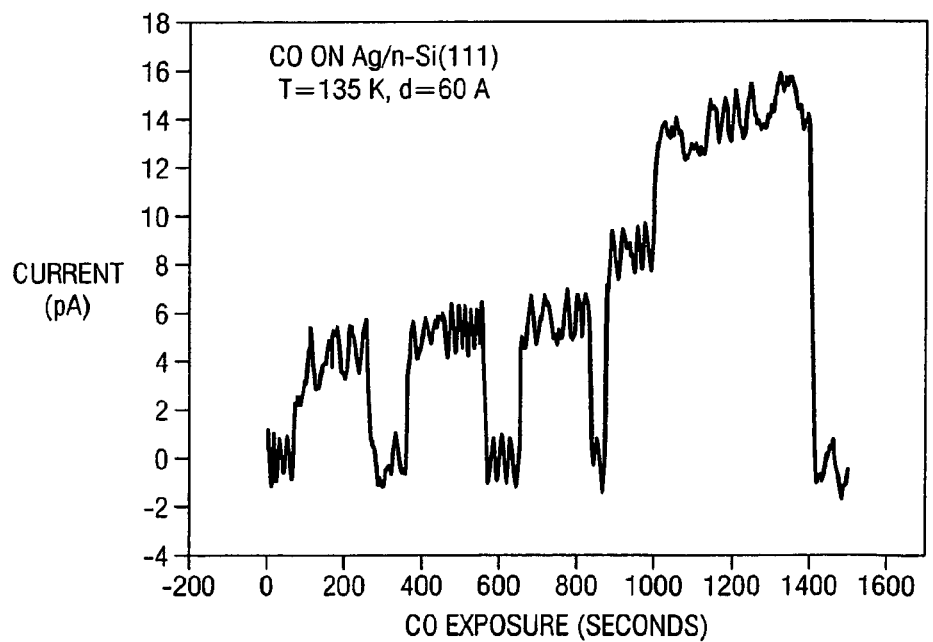
FIG. 4 is a graph of the chemisorption current for a 60 Angstrom Ag/Si (111) sensor at 135K as a function of the time of exposure to CO.
Figure 5:
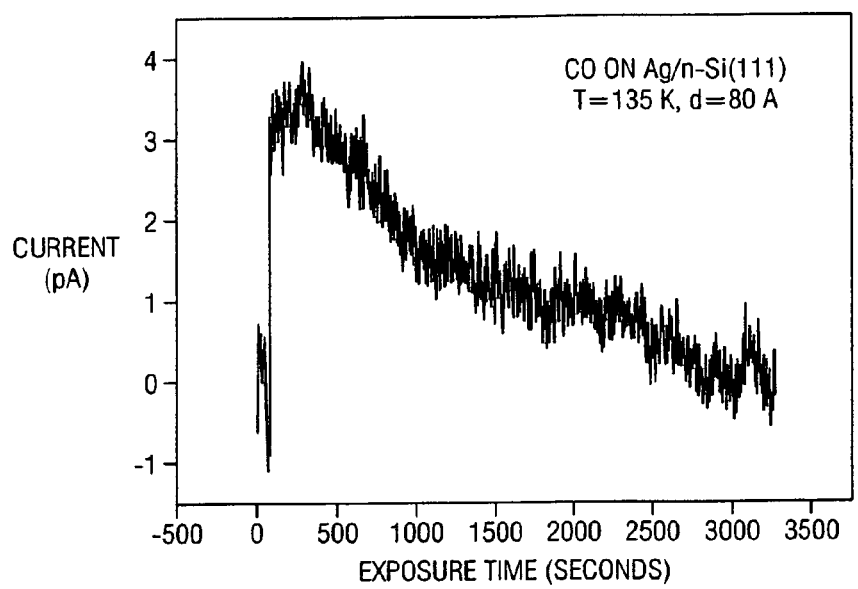
FIG. 5 is a graph of the chemisorption current for an 80 Angstrom Ag/Si (111) sensor at 135K as a function of the time of exposure to CO.
Figure 8:
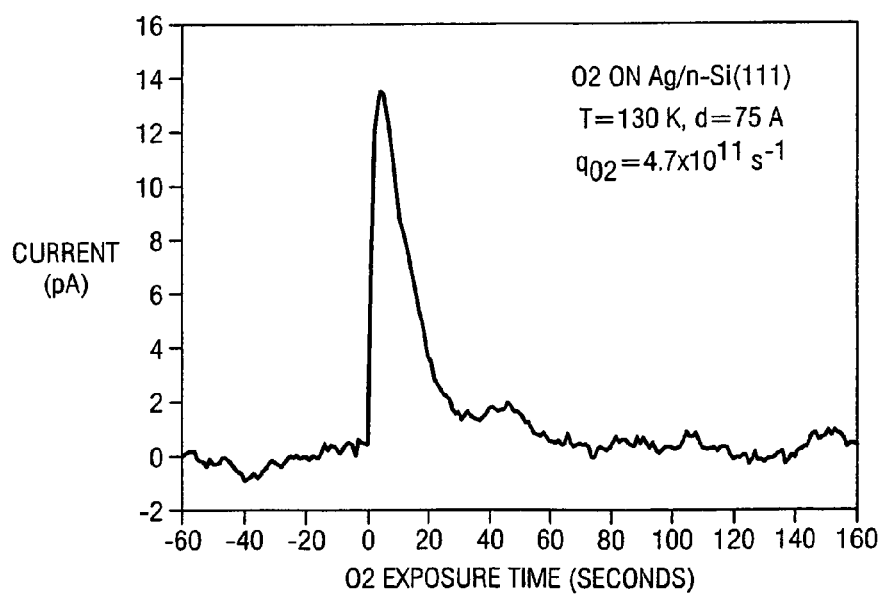
FIG. 8 is a graph of the chemisorption current for molecular oxygen on a 75 Angstrom Ag/Si (111) sensor at 130K as a function of the time of exposure to $O_2$.

For example, it is expected that the chemoelectric phenomena associated with atomic and molecular interactions at metal surfaces will be found to show that chemical reactions at metal surfaces can directly transfer reaction energy to electrons in the metal. The phenomena can thus be utilized as the basis of a new class of solid state sensors. The adsorption induced current of different transition metal-semiconductor combinations will provide a means of systematically varying the relationships between the adsorbate and the metal surface and the electronic environment in the metal at the metal-semiconductor interface, and within the semiconductor. New sensor structures will have improved device sensitivity and allow discrimination of the electron energy with operation at room temperature and above. Bimolecular surface catalyzed reactions in addition to chemisorption is usable for direct excitation of charge carriers during formation of bonds between surface adsorbed species. In addition to the sensor performance and sensitivity for detection of hydrogen, several important adsorbates are possible expressly including CO, $CO_2$, $O_2(O)$, $N_2(N)$, NO, $C_2H_2$, $C_2H_4$, and $C_2H_6$. FIG. 4 shows the chemisorption current as a function of time for CO with a 60 Angstrom Ag/n-silicon (111) sensor of the invention at 135° K. FIG. 5 shows the chemisorption current as a function of time for CO with an 80 Angstrom Ag/n-silicon (111) sensor of the invention at 135K. FIG. 8 shows the response to molecular oxygen. Each adsorbate will have a unique current intensity and rate of signal decay which will allow differentiation of adsorbates.

Figure 6:
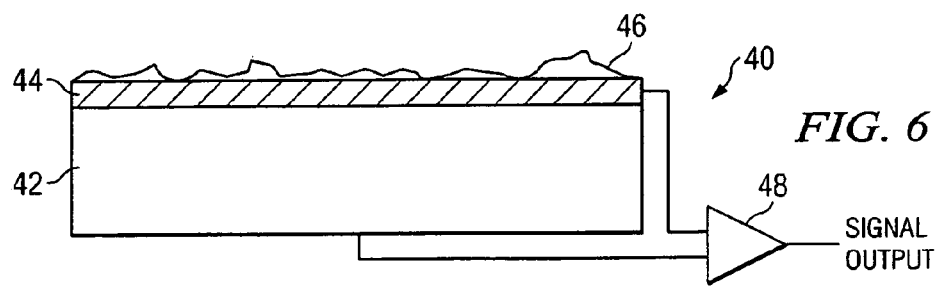
FIG. 6 is a diagrammatic side view of a sensor used for catalytic chemisorption detection.

The sensor response to surface catalyzed reactions of several combinations of these species following absorption are within the scope of the invention expressly including the reactions of $CO+O_2$, $CO+NO$, and $H_2+O_2$. In the sensor 40 of FIG. 6, a catalytic layer 46 is added on top of metal layer 44 disposed on doped silicon layer 42 fabricated in a manner consistent with the teachings of the invention. The chemisorption current is measured by an integrating voltage amplifier 48. Catalytic layer 46 is chosen specifically to catalyze a selected reaction which then directly interacts with metal layer 44 to create a measurable chemicurrent. As shown diagrammatically in FIG. 7, a plurality of sensors 40 of the type shown in FIG. 6 can then be combined in an array, each one of which plurality of sensors 40 has a different catalytic layer 46 to detect a corresponding plurality of different adsorbates through x and y-addressing circuits 50 and current detector 52. In this manner an electronic nose is realized.

The words used in this specification to describe the invention and its various embodiments are to be understood not only in the sense of their commonly defined meanings, but to include by special definition in this specification structure, material or acts beyond the scope of the commonly defined meanings. Thus, if an element can be understood in the context of this specification as including more than one meaning, then its use later in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in later defined claims or that a single element may be substituted for two or more elements in later defined claims.

Insubstantial changes from the claimed subject matter as viewed by a person with ordinary skill in the art, now known or later devised, are expressly contemplated as being equivalently within the scope of the invention. Therefore, obvious substitutions now or later known to one with ordinary skill in the art are defined to be within the scope of the defined elements.

The invention is thus to be understood to include what is specifically illustrated and described above, what is conceptionally equivalent, what can be obviously substituted and also what essentially incorporates the essential idea of the invention.

The invention claimed is:

1. A sensor comprising:
   a semiconductor having a top and a bottom;
   an ultrathin metal film deposited on said top of said semiconductor wherein the interface between said ultrathin metal film and the top of said semiconductor forms a Schottky Barrier;
   at least one oxide layer located on said top of said semiconductor;
   at least one metal pad formed on said oxide layer;
   said ultrathin metal film connected to said at least one metal pad;
   an oxide layer located on said bottom of said semiconductor; and
   a back ohmic contact formed on said oxide layer located on said bottom of said semiconductor.

2. The sensor of claim 1 wherein said ultrathin metal film is deposited on at least one inclination in said one oxide layer on said semiconductor before being connected to said metal pad.

3. The sensor of claim 1 further comprising a catalyst layer located on top of said ultrathin metal film.

4. The sensor of claim 1 further comprising an array of different ultrathin metal films located on an array of different semiconductors.

5. The sensor of claim 1 wherein said sensor is used to detect a chemical located on top of said ultrathin metal film adjacent to said semiconductor.

6. The sensor of claim 1 wherein said sensor is used to detect a chemical reaction on top of said ultrathin metal film adjacent to said semiconductor.

7. The sensor of claim 1 wherein said sensor is used to detect a chemical or chemical reaction on top of said ultrathin metal film adjacent to said semiconductor wherein the presence of the chemical or chemical reaction causes a chemically induced electron-hole production at the Schottky Barrier that creates a measurable chemicurrent.

8. The sensor of claim 1 wherein said sensor uses non-adiabatic energy dissipation during adsorption to detect the presence of a chemical or a chemical reaction on top of said ultrathin metal film adjacent to said semiconductor.

* * * * *

UNITED STATES PATENT AND TRADEMARK OFFICE
CERTIFICATE OF CORRECTION

PATENT NO. : 7,385,271 B2
APPLICATION NO. : 11/119258
DATED : June 10, 2008
INVENTOR(S) : McFarland et al.

It is certified that error appears in the above-identified patent and that said Letters Patent is hereby corrected as shown below:

IN THE SPECIFICATION

Col. 1, line 62, replace "6 mmX6" with --6 mm X 6--.
Col. 3, line 67, replace "(I 11) diodes" with --(111) diodes--.
Col. 4, line 49, replace "coatings, multi-juncition" with --coatings, multi-junction--.
Col. 5, line 23, replace "zarsenic" with --arsenic--.
Col. 5, line 56, replace "C. $H_2O_2$" with --C $H_2O_2$--.
Col. 6, line 33, replace "substrates cooled to 130° K" with --substrates cooled to ~130° K--.
Col. 6, line 40, replace "maintained at 135° K." with --maintained at 135° K--.
Col. 7, line 38, replace "$[\sigma_a(\Theta_s,-\Theta)-\sigma_t\Theta]$" with --$[\sigma_a(\Theta_s,-\Theta)-\sigma_r\Theta]$--.
Col. 7, line 41, replace "($\sigma_a$ and $\sigma_t$)" with --($\sigma_a$ and $\sigma_r$)--.
Col. 7, line 50, replace "($\sigma_a + \sigma_t$)" with --($\sigma_a + \sigma_r$)--.
Col. 7, line 64, replace "films obtained" with --film is obtained--.
Col. 9, line 26, replace "levels, ie.," with --levels, i.e.,--.
Col. 10, line 17, replace "invention at 135 K" with --invention at 135° K--.

Signed and Sealed this

Seventh Day of April, 2009

JOHN DOLL
*Acting Director of the United States Patent and Trademark Office*